(12) United States Patent
Suzuki et al.

(10) Patent No.: US 6,194,567 B1
(45) Date of Patent: Feb. 27, 2001

(54) HALOGENATING AGENT AND PROCESS FOR HALOGENATING HYDROXYL GROUP

(75) Inventors: Daisuke Suzuki; Ryo Kikuchi; Masaru Yasui, all of Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/402,863

(22) PCT Filed: Dec. 10, 1998

(86) PCT No.: PCT/JP98/05579

§ 371 Date: Oct. 13, 1999

§ 102(e) Date: Oct. 13, 1999

(87) PCT Pub. No.: WO99/41214

PCT Pub. Date: Aug. 19, 1999

(30) Foreign Application Priority Data

Feb. 17, 1998 (JP) .................................................. 10-052734

(51) Int. Cl.$^7$ ........................ C07C 17/16; C07C 211/62; C07D 205/08; C07D 213/63
(52) U.S. Cl. ........................ 540/217; 540/354; 540/217; 546/326; 546/327; 554/150; 560/22; 564/278; 568/929; 570/181; 570/185; 570/187
(58) Field of Search .............................. 564/278; 570/181, 570/185, 189; 554/150; 560/22; 546/326, 327; 540/354, 215, 217; 568/929

(56) References Cited

U.S. PATENT DOCUMENTS 3,962,227 6/1976 Chauvette ........................... 260/243
4,568,741 * 2/1986 Livingston et al. ................. 536/16.5

OTHER PUBLICATIONS

Richard F. Dods et al., "The Reaction of Arsenic Trihalides with Nucleosides . . . ", *Journal of Organic Chemistry*; vol. 34, No. 6, p. 1627–1630, 1969.

Richard F. Dods et al., "Halogenation of Nucleosides by (Halomethylene) . . . ", *Tetrahedron Letters*, No. 3, p. 165–168, 1969.

Yoshihara et al., *Conversion of Alcohols to Alkyl Halides Using Iminium Salts*, J. of Syn. Org. Chem., 1980, pp. 746–748.

Al–war et al., *Conversion of N–Acyl–2, 3–dihydro–4–pyridones to 4–Chloro–1, 2–dihydropyridines Using the Vilsmeier Reagents Synthesis of (–)–Conine and (1±)–Lupinine*, J. Org. Chem., 1993, 58, pp. 7732–7739.

Fujisawa et al., *A Conversion Method for the Transformationu of Alcohols to Alkyl Chlorides using N, N–Diphenyl-chlorophenylmethyleniminium Chloride*, Chemistry Letters, 1984, pp. 1173–1174.

Matsumoto, *Replacement of Reactive Phenolic Hydroxyl Groups by Chlorine with Thionyl Chloride and Dimethyl-formamide*, J. Pharm. Soc. of Japan, 1965, 85 (6), 544–546.

* cited by examiner

Primary Examiner—Richard L. Raymond
(74) Attorney, Agent, or Firm—Kubovcik & Kubovcik

(57) ABSTRACT

A halogenating agent of the formula (1) and a method of halogenating hydroxyl group

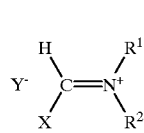

(I)

wherein $R^1$ and $R^2$ are the same or different and are each ethyl, propyl, isopropyl, butyl, isobutyl or allyl; X is chlorine atom or bromine atom; and Y is chlorine ion, bromine ion, dichlorophosphate ion, dibromophosphate ion, chlorosulfonate ion, bromosulfonate ion, chlorooxalate ion or bromooxalate ion.

7 Claims, No Drawings

HALOGENATING AGENT AND PROCESS FOR HALOGENATING HYDROXYL GROUP

This application is a 371 of PCT/JP98/05579, filed Dec. 10, 1998.

TECHNICAL FIELD

The invention relates to a novel halogenating agent and method of halogenating hydroxyl group.

BACKGROUND ART

The novel halogenating agent and halogenating method of the invention enable high purity and high yield production of halogenated aromatic compounds, halogenated heterocyclic compounds and halogenated cholesterol derivatives, each being useful for an intermediate for medicine and agricultural chemical, and also 7-acylamide-3-halocephem derivative useful for general cephem antibiotics used by oral administration.

As a method of halogenating hydroxyl group, it has been conventionally proposed to employ for example dimethyl haloiminium compound and diphenyl haloiminium compound, as a halogenating agent.

More specifically, Journal of Synthetic Organic Chemistry, 1980, 746 discloses a method in which dimethylformamide is reacted with oxalyl dichloride to obtain dimethyl chloroiminium compound, and hydroxyl group bonded to a straight-chain alkyl group is chlorinated by using the above chloroiminium compound. With this method, a 90% yield is achieved, however, such a high yield is not always obtained. Also, the purity of the resulting halogenide is about 80% at the most, and the reaction time is extremely long, namely, 24 hours.

Journal of the Pharmaceutical Society of Japan 85(6), 544–546 (1965) describes a method in which dimethylformamide is reacted with thionyl chloride to form dimethyl chloroiminium compound, and phenolic hydroxyl group is chlorinated by using this compound. This method, however, has the drawbacks that it is not applicable to a compound which has on its benzene ring a substituent liable to be chlorinated, except for hydroxyl group, and that since the reaction system becomes strongly acidic condition, application is limited to one which can be separated outside of the system, as a crystal, immediately after the termination of the reaction, thus being impractical.

Dimethyl haloiminium compound is also used in preparing N-acyl-4-chloro-1,2-dihydropyridine which is an intermediate for alkaloid [J. Org. Chem. (1993) 58, 7732–7739]. This method is, however, impractical because the reaction time is markedly long, namely, three days.

Further, it has been proposed to use dimethyl haloiminium compound in producing a 3-halogenated cephem derivative which is an intermediate for cephalosporin antibiotic used by oral administration (JP-A-116095/1974) With this method, however, the yield is as low as about 60% because the 7-position acyl group is also chlorinated, in addition to the desired 3-position hydroxyl group.

In the meantime, it is known a method with which the hydroxyl group bonded to a straight-chain alkyl group, the hydroxyl group bonded to a straight-chain alkenyl group, and the hydroxyl group of cholesterol, are chlorinated by using diphenyl chloroiminium chloride [Chemistry Letters, pp1173–1174 (1984)]. This method, however, fails to overcome the drawbacks that the reaction time is long, the purity of the resulting halogenide is low, and high yield is not ensured. Furthermore, this method is unsatisfactory for industrial production because the yield does not exceed 90% when chlorinating cholesterol or the compounds containing a double bond or ether linkage within the straight-chain molecules.

An object of the invention is to overcome the drawbacks of long reaction time, unstable yield, low purity, and the formation of by-product obtained by halogenation of other than the desired hydroxyl group, which drawbacks being common to the methods of halogenating hydroxyl group by using dimethyl haloiminium compound or diphenyl haloiminium compound.

DISCLOSURE OF THE INVENTION

The invention relates to halogenating agents of the following formula (1), and a method of halogenating hydroxyl group

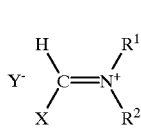

(I)

wherein $R^1$ and $R^2$, which may be the same or different, each is ethyl, propyl, isopropyl, butyl, isobutyl or allyl; X is chlorine atom or bromine atom; and Y is chlorine ion, bromine ion, dichlorophosphate ion, dibromophosphate ion, chlorosulfonate ion, bromosulfonate ion, chlorooxalate ion or bromooxalate ion.

In accordance with the invention, compounds obtained by halogenation of hydroxyl group can be produced at high yield and high purity in a short period of time.

After the present inventor conducted intensive research to solve the problems in the prior art, it has been found to overcome a variety of drawbacks acknowledged in the case of using dimethyl haloiminium compound by conducting halogenation of hydroxyl group by using a specific dialkylhaloiminium compound, namely, the compound in which alkyl part has 2 to 4 carbon atoms, thereby enabling to produce the desired halogenide at high yield and high purity in a short period of time.

More specifically, when the halogenating agent of the invention is used, only hydroxyl group is selectively halogenated, irrespective of the structure of a hydroxyl group containing compound and the kind of a substituent other than hydroxyl group. For example, in the reaction with 3-hydroxycephem compound described in JP-A-116095/1974, the acyl group at the 7-position and lactam part are not halogenated, and only the hydroxyl group at the 3-position is selectively halogenated. Therefore, the desired halogenide can be produced at high yield and high purity, and the reaction time is short.

It has also been found by the inventor that the combined use of a dimethyl haloiminium compound and a specific organic sulfur compound can also overcome the drawbacks of dimethyl haloiminium compound and only hydroxyl group is selectively halogenated, thus enabling to produce the desired halogenide at high yield and high purity in a short period of time.

Description will be made of the respective groups indicated in the present specification.

Examples of halogen atom are chlorine atom and bromine atom.

Examples of $C_1$–$C_4$ alkyl group are straight-chain or branched-chain alkyl groups, such as methyl, ethyl, n-propyl, isopropyl, n-butyl, isobutyl, sec-butyl and tert-butyl.

Examples of $C_2$–$C_8$ alkenyl group are straight-chain or branched-chain alkenyl groups, such as vinyl, propenyl, butenyl, pentenyl, hexenyl, isopropenyl, isobutenyl, isopentenyl, octenyl and isoprenyl.

Examples of monocyclic or polycyclic aromatic hydrocarbon group are phenyl group, naphthalene group and anthracene group. Examples of monocyclic or polycyclic heterocyclic hydrocarbon group are furyl group, pyrrolyl group, thienyl group, oxazolyl group, imidazolyl group, thiazolyl group, pyridyl group, pyrazyl group, pyridazyl group, morpholinyl group, quinolyl group, isoquinolyl group, indole group, indolizyl group, penicillin residue and cephalosporin residue. Examples of steroid residue are androsterone residue, testosterone residue and cholesterol residue.

Examples of $C_1$–$C_{15}$ alkyl group are straight-chain, branched-chain or cyclic alkyl groups, such as methyl, ethyl, propyl, butyl, isopropyl, isobutyl, tert-butyl, hexyl, cyclohexyl and pentadecanyl.

Examples of substituted oxycarbonyl group are bromobutoxycarbonyl, methoxycarbonyl, ethoxycarbonyl, propoxycarbonyl, butoxycarbonyl, benzyloxycarbonyl and allyloxycarbonyl.

Examples of acyl group are formyl, acetyl, propionyl, butyryl, valeryl, benzoyl, toluoyl and naphthoyl.

Exemplary of the protected amino group are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Further, also are included groups of the formula (A)

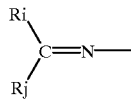

(A)

wherein Ri and Rj are same or different and each a hydrogen atom, $C_1$–$C_{15}$ alkyl group, aromatic hydrocarbon group or heterocyclic hydrocarbon group, or may bond together to form a cyclic group.

Examples of $C_1$–$C_{15}$ alkyl group, aromatic hydrocarbon group and heterocyclic hydrocarbon group are the same as given above. Examples of the aforesaid cyclic group are $C_4$–$C_8$ cycloalkyl group (e.g., cyclobutyl, cyclohexyl, cyclooctyl, etc), including carbon bonded to N, and aromatic groups (e.g., phenyl, tolyl, naphthyl, etc.)

Examples of lower alkoxy group are straight-chain or branched-chain $C_1$–$C_4$ alkoxy group, such as methoxy, ethoxy, n-propoxy, isopropoxy, sec-butoxy and tert-butoxy. Examples of cyclic amino protecting group are phthaloyl group and nitrophthaloyl group. Examples of the protective group for carboxylic acid are allyl group, benzyl group, p-methoxybenzyl group, p-nitrobenzyl group, diphenylmethyl group, trichloromethyl group, trichloroethyl group and tert-butyl group, in addition to a variety of groups as described in the fifth chapter of the aforesaid literature (pages 152–192).

In the invention, the dialkyl haloiminium compounds of the formula (1) are used as a halogenating agent for hydroxyl group. Examples of the dialkyl haloiminium compound are diethyl haloiminium compound, diisopropyl haloiminium compound, dibutyl haloiminium compound, diallyl haloiminium compound, methylethyl haloiminium compound, ethylpropyl haloiminium compound, ethylbutyl haloiminium compound and ethylpentyl haloiminium compound. Of these, preferred is dialkyl haloiminium compound in which $R^1$ and $R^2$ are the same group, and particularly preferred is diethyl haloiminium compound. The dialkyl haloiminium compounds may be used singly or in a combination of at least two of them.

The dialkyl haloiminium compounds or diallyl haloiminium compounds of the formula (1) (hereinafter both are simply referred to as dialkyl haloiminium compounds), can be produced, for example, by allowing dialkylformamide or diallylformamide of the following formula to react with a halogenating agent in an organic solvent

wherein $R^1$ and $R^2$ are the same or different and are each same as given above.

The organic solvent used herein is not limited specifically insofar as it does not cause adverse effect on the reaction between the dialkylformamide or diallylformamide and the halogenating agent. There are, for example, lower alkyl esters of lower carboxylic acid, such as methyl formate, ethyl formate, propyl formate, butyl formate, methyl acetate, ethyl acetate, propyl acetate, butyl acetate, methyl propionate and ethyl propionate; ketones such as acetone, methyl ethyl ketone, methyl propyl ketone, methyl butyl ketone, methyl isobutyl ketone and diethyl ketone; ethers such as diethyl ether, ethyl propyl ether, ethyl butyl ether, dipropyl ether, diisopropyl ether, dibutyl ether, methyl cellosolve and dimethoxyethane; cyclic ethers such as tetrahydrofuran, dioxane and dioxolane; nitriles such as acetonitrile, propionitrile, butyronitrile, isobutyronitrile and valeronitrile; aromatic hydrocarbons such as benzene, toluene, xylene, chlorobenzene and anisole; halogenated hydrocarbons such as dichloromethane, chloroform, dichloroethane, trichloroethane, dibromoethane, propylene dichloride and carbon tetrachloride; aliphatic hydrocarbons such as pentane, hexane, heptane and octane; and cycloalkanes such as cyclopetane, cyclohexane, cycloheptane and cyclooctane. They may be used singly or in a combination of at least two of them. If desired, these organic solvents may be previously dehydrated prior to use by molecular sieves, for example. Although the amount of organic solvent is not limited specifically, it is usually about 1 to 100 liters, preferably about 5 to 50 liters, per 1 kg of the dialkylformamide or diallylformamide.

As a halogenating agent, any one known in the art can be used. There are, for example, phosgene, oxalyl dichloride, thionyl chloride, phosphorus pentachloride, phosphorous trichloride, phosphorus oxychloride, carbonyl dibromide, oxalyl bromide, thionyl bromide, phosphorous bromide and phosphorus oxybromide. The halogenating agents can be used singly or in a combination of at least two of them. Although the amount of halogenating agent is not specifically limited, it is usually 0.5 to 10 equivalents to dialkyl formamide or diallyl formamide. If necessary, the halogenating agent may be further added until the dialkyl formamide or diallyl formamide is exhausted.

The above reaction is usually conducted at temperatures of about −78 to 60° C., preferably about 0 to 30° C., and the reaction is usually completed in about 0.5 to 20 hours, preferably about 0.5 to 8 hours. After the termination of the reaction, the reaction mixture is purified by the usual means such as concentration, thereby isolating the halogenating agent of the invention (dialkyl haloiminium compound). Alternatively, the reaction mixture containing the halogenating agent of the invention can be directly used, without purification, for the halogenating reaction of hydroxyl group.

A method of halogenating hydroxyl group according to the invention will be described. In the invention, halogenides of the following formula (3) (hereinafter referred to as "halogenide (3)") are produced by reacting at least one of the halogenating agents of the formula (1) (hereinafter referred to as "halogenating agent (1)") with a hydroxyl group containing compound of the following formula (2) (hereinafter referred to as "hydroxyl containing compound (2)") in an organic solvent $$A-OH \quad (2)$$

wherein A is a straight-chain or branched-chain alkyl group which may be substituted, a straight-chain or branched-chain alkenyl group which may be substituted, a monocyclic or polycyclic aromatic residue which may be substituted, a steroid residue, or a monocyclic or polycyclic heterocyclic residue which may be substituted $$A-X \quad (3)$$

wherein A and X are the same as above.

The hydroxyl group containing compound is not specifically limited, and any organic compounds which has a hydroxyl group in the molecule can be used. There are, for example, the following compounds (5) through (11). Examples of substituent are aryl group and lower alkoxycarbonyl group. Examples of the lower alkoxy group of the lower alkoxycarbonyl group are alkoxy group having 1 to 4 carbon atoms.

Compound (5): Sraight-chain or branched-chain alkyl alcohol in which alkyl part has 1 to 15 carbon atoms and may be substituted.

Compound (6): Straight-chain or branched-chain alkenyl alcohol in which alkenyl part has 2 to 8 carbon atoms and may be substituted.

Compound (7): 3-β-cholesterol

Compound (8): Compounds of the formula (8):

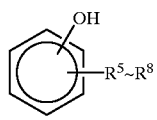

wherein $R^5$ to $R^8$ are the same or different and are each hydrogen atom, $C_1$–$C_4$ lower alkyl group, nitro group, hydroxyl group, carboxyl group, or substituted oxycarbonyl group.

Compound (9): Compounds of the formulas (9a) to (9c):

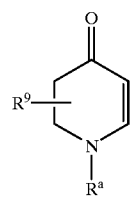

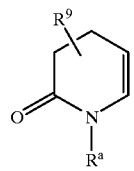

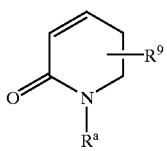

wherein $R^9$ is a straight-chain or branched-chain $C_1$–$C_{15}$ alkyl group, a straight-chain or branched-chain $C_2$–$C_8$ alkenyl group, cyclohexyl group, or phenyl group; and Ra is hydrogen atom or a substituted oxycarbonyl group.

Compound (10): Compounds of the formula (10):

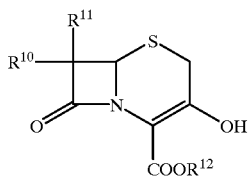

wherein $R^{10}$ is hydrogen atom, amino group, or a protected amino group; $R^{11}$ is hydrogen atom or lower alkoxy group, alternatively, $R^{10}$ and $R^{11}$ may be bonded with each other to form a cyclic amino protecting group; and $R^{12}$ is hydrogen atom or carboxylic acid protecting group.

Compound (11): Compounds of the formula (11):

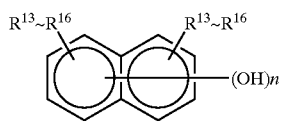

(11)

wherein $R^{13}$ to $R^{16}$ are the same or different and are each hydrogen atom, $C_1$–$C_4$ lower alkyl group, nitro group, hydroxyl group, carboxyl group, or a substituted oxycarbonyl group; and n is 1 or 2.

Of these, Compounds (5) to (10) are preferred, Compounds (7) to (10) are more preferred, Compounds (9) and (10) are most preferred, and Compound (10) is the best.

As an organic solvent, those which are used in producing the halogenating agent (1) of the invention (the above-mentioned ones) can be used. It is also possible to use amides containing dimethylacetoamide, dimethylimidazolidinone and a cyclic amide such as N-methyl-2-pyrrolidone. They can be used solely or in a combination of at least two of them. The amount of organic solvent is not specifically limited and can be selected appropriately from a wide range. It is, however, usually about 1 to 200 liters, preferably about 5 to 20 liters, per 1 kg of the hydroxyl group containing compound (2).

The amount of the halogenating agent (1) is not specifically limited and can be selected suitably from a wide range. It is, however, usually 0.1 to 10 equivalents, preferably 0.5 to 2.0 equivalents, to the hydroxyl group containing compound (2). The halogenating compound (1) may be added, as required, until the hydroxyl group containing compound (2) in the reaction system is exhausted.

The above reaction is conducted with or without stirring, usually at temperatures of about −78 to 60° C., preferably about 0 to 30° C., and the reaction is usually terminated in about 0.5 to 20 hours, preferably about 0.5 to 8 hours. If necessary, the reaction can also be conducted in a sealed container or in the presence of an inert gas, e.g., nitrogen gas. The resulting halogenide (3) is easily isolated by the usual purification operation, such as concentration, distillation, chromatography and crystallization.

In another feature of the invention, the halogenide (3) can be produced by allowing the hydroxyl group containing compound (2) to react with at least one kind selected from the group consisting of the halogenating agents of the formula (1) and those of the formula (4) (hereinafter referred to as "halogenating agent (4)"), and at least one kind selected from the group consisting of lower alkyl sulfone, lower alkenyl sulfone, aryl sulfone and heterocyclic sulfone, in an organic solvent at the same time

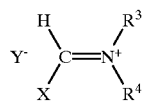

(4)

wherein $R^3$ and $R^5$ are methyl or phenyl; and X and Y are the same as above.

This reaction is particularly effective for the halogenation of Compound (10).

The kind and amount of the organic solvent used herein, the amount of the halogenating agent, and the reaction conditions such as the reaction temperature and time, may be the same as in the case where the halogenide (3) is produced by using the halogenating agent (1) alone.

Examples of the lower alkyl sulfone, lower alkeny sulfone, aryl sulfone and heterocyclic sulfone (unless otherwise stated, hereinafter referred to as "sulfones") are dimethyl sulfone, diethyl sulfone, dipropyl sulfone, diisopropyl sulfone, dibutyl sulfone, diisobutyl sulfone, methylethyl sulfone, methylpropyl sulfone, methylbutyl sulfone, ethylpropyl sulfone, ethylbutyl sulfone, divinyl sulfone, dipropenyl sulfone, vinylpropenyl sulfone, diphenyl sulfone, ditoluyl sulfone and dipyridyl sulfone. Solfones can be used solely or in a combination of at least two of them. The amount of solfones is not specifically limited and can be suitably selected from a wide range. It is, however, usually from about 0.1 to 20 mole %, preferably about 3 to 10 mole %, to the hydroxyl group containing compound (2).

In another aspect of the invention, there are provided halogenides by that, using dialkylformamide or diallylformamide itself as an organic solvent, a known halogenating agent is reacted therewith to generate the halogenating agent (1) and/or halogenating agent (4) of the invention within the reaction system, and the hydroxyl group containing compound (2) is then added into the reaction system. When only the halogenating agent (4) is generated in the reaction system, it is necessary to add sulfones. When the halogenating agent (1) coexists, solfones may be optionally added. In this case, the reaction conditions, such as the amount of the dialkylformamide or diallylformamide, the amount of the halogenating agent (1) and/or halogenating agent (4), the kind and amount of sulfones, and the reaction temperature and time, may be the same as stated earlier. If necessary, the reaction can also be conducted in a sealed container or in the presence of an inert gas, e.g., nitrogen gas. The resulting halogenide (3) is easily isolated by the usual purification operation, such as concentration, distillation, chromatography and crystallization.

BEST MODE OF CARRYING OUT THE INVENTION

The following Preparation Examples (the preparation of the halogenating agent (1) or the halogenating agent (4)) Examples and Comparative Examples are being supplied to further define the present invention.

PREPARATION EXAMPLE 1

The atmosphere of a 300-ml four-necked flask equipped with a thermometer, a calcium chloride tube and a stirrer was replaced with argon gas, and 50 ml of methylene chloride and 4.3 g of N,N-diethylformamide were placed in the flask and then stirred with ice cooling. Then, 5.23 ml of oxalyl dichloride was added by a syringe and further stirred with ice cooling for one hour. The reaction mixture was subjected to vacuum concentration and then crystallization with 50 ml of ethyl ether, to prepare 6.4 g of N,N-diethylchloroiminium chloride (1a)

$^1$H NMR(CDCl$_3$) δ 1.45(t, J=7.4 Hz, 6H), 4.23(brs, 4H) 10.94(s, 1H)

PREPARATION EXAMPLE 2

The procedure was conducted in the same manner as in Preparation Example 1 except that 6.0 g of N,N-di-n-propylformamide was used in place of 4.3 g of N,N-diethylformamide, to prepare 8.8 g of N,N-di-n-propylchloroiminium chloride (1b).

$^1$H NMR(CDCl$_3$) δ 1.39(t, J=7.4 Hz, 6H), 3.75(m, 2H) 3.95(m, 2H), 4.23(t, J=7.4 Hz, 2H), 4.44(t, J=7.4 Hz, 2H) 10.71(s, 1H)

PREPARATION EXAMPLE 3

The procedure was conducted in the same manner as in Preparation Example 1 except that 6.1 g of N,N- diisopropylformamide was used in place of 4.3 g of N,N-diethylformamide, to prepare 8.7 g of N,N-diisopropylchloroiminium chloride (1c).

$^1$H NMR(CDCl$_3$) δ 1.41(m, 12H), 3.81 (m, 1H), 4.20(m, 1H) 10.93(s, 1H)

PREPARATION EXAMPLE 4

The procedure was conducted in the same manner as in Preparation Example 1 except that 7.6 g of N,N-di-n-butylformamide was used in place of 4.3 g of N,N-diethylformamide, to obtain 11.3 g of N,N-di-n-butylchloroiminium chloride (1d).

$^1$H NMR(CDCl$_3$) δ 1.37(t, J=7.4 Hz, 6H), 3.89(m, 8H), 4.14(t, J=7.4 Hz, 4H), 10.75(s, 1H)

PREPARATION EXAMPLE 5

The procedure was conducted in the same manner as in Preparation Example 1 except that 5.7 g of N,N-diallylformamide was used in place of 4.3 g of N,N-diethylformamide, to prepare 8.5 g of N,N-diallylchloroiminium chloride (1e).

$^1$H NMR(CDCl$_3$) δ 3.56(d, J=7.5 Hz, 4H), 5.35(m, 4H), 6.10(m, 2H), 10.94(s, 1H)

PREPARATION EXAMPLE 6

Into a dried 50-ml eggplant type flask was placed 35 ml of dehydrated diethylformamide and 4.2 g of phosphorus oxychloride was then added thereto at room temperature. The mixture was stirred at 30° C. for one hour, to prepare a solution of diethyl chloroiminium chloride compound in diethylformamide.

PREPARATION EXAMPLE 7

The procedure was conducted in the same manner as in Preparation Example 6 except that dehydrated dimethylformamide was used in place of the dehydrated diethylformamide, to prepare a solution of dimethyl chloroiminium chloride compound in dimethylformamide.

EXAMPLE 1

Preparation of diphenylmethyl(6R, 7R)-7-phenylacetamide-3-chloro-8-oxo-5-thia-1-azabicyclo[4.2.0]octo-2-ene-2-carboxylate (3a):

Into a 300-ml four-necked flask equipped with a thermometer, a calcium chloride tube and a stirrer was placed 12.5 g of diphenylmethyl(6R, 7R)-7-phenylacetamide-3-hydroxy-8-oxo-5-thia-1-azabicyclo[4.2.0]octo-2-ene-2-carboxylate (2a) (purity: 90%, 22.5 millimole) and 70 ml of dehydrated diethylformamide was then added thereto and dissolved with stirring at room temperature. To this solution, the diethylformamide solution of diethyl chloroiminium chloride compound in Preparation Example 6 was added with ice cooling. After the reaction mixture was further stirred at room temperature for 6 hours, it was poured into 1 liter of ice water. The separated crystal was filtered and then washed with a small amount of water, followed by vacuum drying to prepare 11.9 g of the desired compound (3a) (purity: 94% yield: 96%).

$^1$H NMR(DMSO) δ ppm 3.52(ABq., 2H, J=12 Hz), 3.96(ABq., 2H, J=15 Hz), 5.21(d, 1H, 5.5 Hz), 5.78(dd, 1H, 7.5 Hz, 5.5 Hz), 6.97(s, 1H), 7.18~7.49 (m, 15H), 9.20 (d, 1H, 7.5 Hz)

EXAMPLE 2

Preparation of Compound (3a):

Into a 300-ml four-necked flask equipped with a thermometer, a calcium chloride tube and a stirrer was placed 12.5 g of Compound (2a) (purity: 90%, 22.5 millimole) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 1, to prepare 11.5 g of the desired compound (3a) (purity: 95%, yield: 94%). This was identical with Example 1 in $^1$H NMR (DMSO) spectrum.

EXAMPLE 3

Preparation of p-methoxybenzyl(6R, 7R)-7-phenylacetamide-3-chloro-8-oxo-5-thia-1-azabicyclo[4.2.0]octo-2-ene-2-carboxylate (3b):

Into a 300-ml four-necked flask equipped with a thermometer, a calcium chloride tube and a stirrer was placed 11.4 g of p-methoxybenzyl(6R, 7R)-7-phenylacetamide-3-hydroxy-8-oxo-5-thia-1-azabicyclo[4.2.0]octo-2-ene-2-carboxylate (2b) (purity: 92%, 23.1 millimole) and 70 ml of dehydrated diethylformamide was then added thereto and dissolved with stirring at room temperature. To this solution, the diethylformamide solution of diethylchloroiminium chloride compound in Preparation Example 6 was added with ice cooling. The reaction mixture was treated in the same manner as in Example 1, to prepare 11.0 g of the desired compound (3b) (purity: 96%, yield: 97%).

$^1$H NMR(CDCl$_3$) δ ppm 3.42(d, 1H, J=17.8 Hz), 3.72(d, 1H, J=17.8 Hz), 3.58(d, 1H, J=16.4 Hz), 3.64(d, 1H, J=16.4 Hz), 3.79(s, 3H), 4.96(d, 1H, 5.1 Hz), 5.21(s, 2H), 5.79(dd, 1H, 9.2 Hz, 5.1 Hz), 6.39(d, 1H, 9.2 Hz), 6.82~7.40(m, 9H)

EXAMPLE 4

Preparation of Compound (3b):

Into a 300-ml four-necked flask equipped with a thermometer, a calcium chloride tube and a stirrer was placed 11.4 g of Compound (2b) (purity: 92%, 23.1 millimole) and 70 ml of dehydrated dimethylformamide was then added with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 1, to prepare 10.8 g of the desired compound (3b) (purity: 96% yield: 95%). This was identical with Example 3 in $^1$H NMR(CDCl$_3$) spectrum.

EXAMPLE 5

Preparation of diphenylmethyl(6R, 7R)-7-phthalimide-3-chloro-8-oxo-5-thia-1-azabicyclo[4.2.0]octo-2-ene-2-carboxylate (3c):

Into a 300-ml four-necked flask equipped with a thermometer, a calcium chloride tube and a stirrer was placed 12.7 g of diphenylmethyl(6R, 7R)-7-phthalimide-3-hydroxy-8-oxo-5-thia-1-azabicyclo[4.2.0]octo-2-ene-2-carboxylate (2c) (purity: 95%, 23.8 millimole) and 70 ml of dehydrated diethylformamide was then added thereto and dissolved with stirring at room temperature. To this solution, the diethylformamide solution of diethyl chloroiminium chloride compound in Preparation Example 6 was added with ice cooling. The reaction mixture was treated in the same manner as in Example 1, to prepare 12.5 g of the desired compound (3c) (purity: 93%, yield: 92%

$^1$H NMR(CDCl$_3$) δ 4.19~4.90(m, 2H), 4.625(ABq., 2H, J=5.5 Hz), 5.975(d, 1H, J=4.8 Hz), 6.970(s, 1H), 7.21~7.62 (m, 10H), 7.76~7.94(m, 4H)

EXAMPLE 6

Preparation of Compound (3c):

Into a 300-ml four-necked flask equipped with a thermometer, a calcium chloride tube and a stirrer was placed 12.7 g of Compound (2c) (purity: 95%, 23.8 millimole) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 1, to prepare 13.1 g of the desired compound (3c) (purity: 90%, yield: 93%). This was identical with Example 5 in $^1$H NMR (CDCl$_3$) spectrum.

EXAMPLE 7

Preparation of Compound (3a):

Into a 300-ml four-necked flask equipped with a thermometer, a calcium chloride tube and a stirrer was placed 12.5 g of Compound (2a) (purity: 90%, 22.5 millimole) and 70 ml of dehydrated dimethylformamide was then added thereto and dissolved with stirring at room temperature. To this solution, the diethylformamide solution of diethyl chloroiminium chloride compound in Preparation Example 6 and 118 mg (5 mole %) of dimethyl sulfone were added with ice cooling. The reaction mixture was treated in the same manner as in Example 1, to prepare 12.2 g of the desired compound (3a) (purity: 92%, yield: 96%). This was identical with Example 1 in $^1$H NMR(DMSO) spectrum.

EXAMPLE 8

Preparation of Compound (3a):

Into a 300-ml four-necked flask equipped with a thermometer, a calcium chloride tube and a stirrer was placed 12.5 g of Compound (2a) (purity: 90%, 22.5 millimole) and 70 ml of dehydrated dimethylformamide was then added thereto and dissolved with stirring at room temperature. To this solution, the dimethylformamide solution of dimethyl chloroiminium chloride compound in Preparation Example 7 and 154 mg (5 millimole %) of diethyl sulfone were added with ice cooling. The reaction mixture was treated in the same manner as in Example 1, to prepare 11.6 g of the desired compound (3a) (purity: 95%, yield: 95%). This was identical with Example 1 in $^1$H NMR(DMSO) spectrum.

EXAMPLE 9

Preparation of Compound (3a):

Into a 300-ml four-necked flask equipped with a thermometer, a calcium chloride tube and a stirrer was placed 12.5 g of Compound (2a) (purity: 90%, 22.5 millimole) and 70 ml of dehydrated dimethylformamide was then added thereto and dissolved with stirring at room temperature. To this solution, the dimethylformamide solution of dimethyl chloroiminium chloride compound in Preparation Example 7 and 274 mg (5 mole %) of diphenyl sulfone were added with ice cooling. The reaction mixture was treated in the same manner as in Example 1, to prepare 11.8 g of the desired compound (3a) (purity: 90%, yield: 91%). This was identical with Example 1 in $^1$H NMR (DMSO) spectrum.

EXAMPLE 10

Preparation of N-[(benzyloxy)carbonyl]-4-chloro-2-cyclohexyl-1,2-dihydropyridine (3d)

Into a 300-ml four-necked flask equipped with a thermometer, a calcium chloride tube and a stirrer was placed 7.2 g (23 millimole) of N-[(benzyloxy)carbonyl]-2-cyclohexyl2,3-dihydro-4-pyridone (2d) and 70 ml of dehydrated diethylformamide was then added thereto and dissolved with stirring at room temperature. To this solution, the diethylformamide solution of diethyl chloroiminium chloride compound in Preparation Example 6 was added with ice cooling. The reaction mixture was further stirred at room temperature for 6 hours, and this was poured into 1 liter of ice water and then extracted with 50 ml of ethyl acetate. After drying with anhydrous magnesium sulfate, this was subjected to concentration at reduced pressure and then purified with silicagel column chromatography, to prepare 7.7 g of the desired compound (3d) (purity: 97%, yield: 98%), as a colorless transparent oil. This was identical with standard sample in $^1$H NMR(CDCl$_3$) spectrum.

EXAMPLE 11

Preparation of Compound (3d):

Into a 300-ml four-necked flask equipped with a thermometer, a calcium chloride tube and a stirrer was placed 7.2 g of Compound (2d) (23 millimole) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 10, to prepare 7.6 g of the desired compound (3d) (purity: 96%, yield: 96%), as a colorless transparent oil. This was identical with standard sample in $^1$H NMR(CDCl$_3$) spectrum.

EXAMPLE 12

Preparation of 2-chloro-5-tert-butyl-1,3-dinitrobenzene (3e):

Into a 300-ml four-necked flask equipped with a thermometer, a calcium chloride tube and a stirrer was placed 5.5 g (23 millimole) of 4-tert-butyl-2,6-dinitrophenol (2e) and 70 ml of dehydrated diethylformamide was then added thereto and dissolved with stirring at room temperature. To this solution, the diethylformamide solution of diethyl chloroiminium chloride compound in Preparation Example 6 was added with ice cooling. After the reaction mixture was further stirred at room temperature for 6 hours, it was poured into 1 liter of ice water. The separated crystal was filtered and then washed with a small amount of cooled methanol, followed by vacuum drying to prepare 6.1 g of the desired compound (3e) (purity: 95%, yield: 97%). Its melting point (113 to 115° C.) was similar to that of standard sample (115° C.).

EXAMPLE 13

Preparation of Compound (3e):

Into a 300-ml four-necked flask equipped with a thermometer, a calcium chloride tube and a stirrer was placed 5.5 g of Compound (2e) (23 millimole) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 12, to prepare 6.0 g of the desired compound (3e) (purity: 92%, yield: 92%). This was identical with standard sample in melting point and elementary analysis.

EXAMPLE 14

Preparation of 3-α-chlorocholestane (3f)

Into a 300-ml four-necked flask equipped with a thermometer, a calcium chloride tube and a stirrer was placed 8.9 g (23 millimole) of 3-β-cholestanol (2f) and 70 ml of dehydrated dimethylformamide was then added thereto and dissolved with stirring at room temperature. To this solution, the diethylformamide solution of diethyl chloroiminium chloride compound in Preparation Example 6 was added with ice cooling. The reaction mixture was treated in the same manner as in Example 1, to prepare 9.5 g of the desired compound (3f) (purity: 90%, yield: 91%). Its melting point (105 to 106° C.) was similar to that of standard sample (104° C.)

EXAMPLE 15

Preparation of Compound (3f):

Into a 300-ml four-necked flask equipped with a thermometer, a calcium chloride tube and a stirrer was placed 8.9 g (23 millimole) of Compound (2f) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were added with ice cooling. The reaction mixture was treated in the same manner as in Example 1, to prepare 9.6 g of the desired compound (3f) (purity: 93%, yield: 95%). This was identical with standard sample in melting point and elementary analysis.

EXAMPLE 16

Preparation of 4,4-ethylenedioxypentane-1-chloride (3g):

Into a 300-ml four-necked flask equipped with a thermometer, a calcium chloride tube and a stirrer was placed 3.4 g (23 millimole) of 4,4-ethylenedioxypentane-1-ol (2g) and 70 ml of dehydrated dimethylformamide was then added thereto and dissolved with stirring at room temperature. To this solution, the diethylformamide solution of diethyl chloroiminium chloride compound in Preparation Example 6 was added with ice cooling. The reaction mixture was treated in the same manner as in Example 10, to prepare 3.9 g of the desired compound (3g) (purity: 96%, yield: 98%), as a colorless transparent oil. This was identical with standard sample in $^1$H NMR(CDCl$_3$) spectrum.

EXAMPLE 17

Preparation of Compound (3g):

Into a 300-ml four-necked flask equipped with a thermometer, a calcium chloride tube and a stirrer was placed 3.4 g (23 millimole) of Compound (2g) and 70 ml of dehydrated dimethylformamide was then added thereto and dissolved with stirring at room temperature. To this solution, the dimethylformamide solution of dimethyl chloroiminium chloride compound in Preparation Example 7 and 118 mg (5 mole %) of dimethyl sulfone were then added with ice cooling. The reaction mixture was treated in the same manner as in Example 10, to prepare 3.8 g of the desired compound (3g) (purity: 94%, yield: 95%), as a colorless transparent oil. This was identical with standard sample in $^1$H NMR(CDCl$_3$) spectrum.

EXAMPLES 18 TO 30

The halogenating reaction was conducted in the same manner as in Example 1 except for the use of a starting material shown below and a chlorinating agent shown in Table 1, and the employment of reaction conditions shown in Table 2, to prepare the desired halogenide.

Starting material

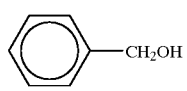

I

II n-C$_{11}$H$_{23}$OH

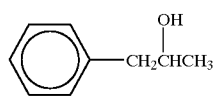

III

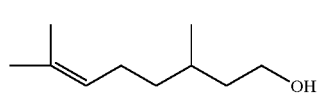

IV

V

CH$_3$OC(CH$_2$)$_{14}$OH

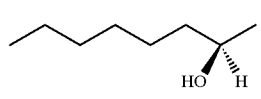

VI

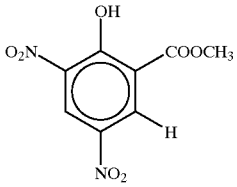

VII

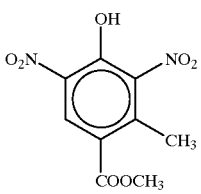

VIII

| Ex. | Starting material | Solvent | Reaction condition | Halogenating agent |
|-----|-------------------|---------|--------------------|--------------------|
| 18 | (I) | dichloromethane | RT × 3 hr | (1f) |
| 19 | (II) | chloroform | RT × 5 hr | (1c) |
| 20 | (III) | chloroform | RT × 5 hr | (1g) |
| 21 | (IV) | dichloromethane | RT × 5 hr | (1a) |
| 22 | (V) | dichloromethane | RT × 5 hr | (1a) |
| 23 | (VI) | dichloromethane | RT × 5 hr | (1a) |
| 24 | (VII) | tetrahydrofuran | RT × 3 hr | (1d) |
| 25 | (VIII) | tetrahydrofuran | RT × 3 hr | (1d) |
| 26 | (IX) | diethylformamide | RT × 6 hr | (1a) |
| 27 | (X) | trichlene | RT × 10 hr | (1a) |
| 28 | (XI) | dimethylimidazolidinone | RT × 7 hr | (1a) |
| 29 | (XII) | N-methyl-pyrrolidone | RT × 7 hr | (1a) |
| 30 | (XIII) | tetrahydrofuran | RT × 6 hr | (1a) |

RT: Room temperature

Product

Example

-continued

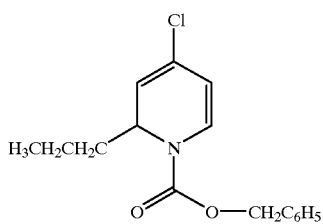

26

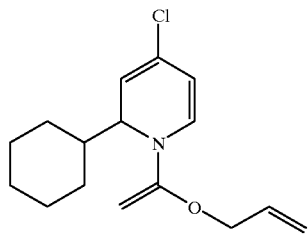

27

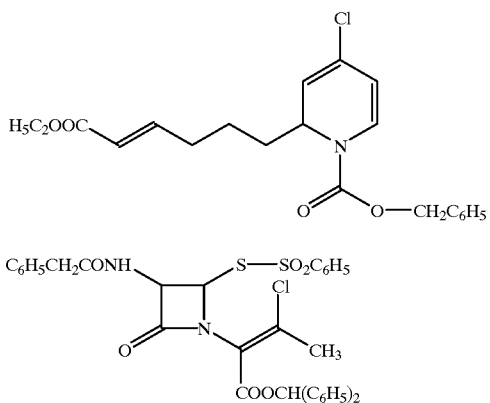

28

29

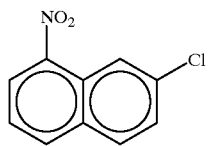

30

COMPARATIVE EXAMPLE 1

Preparation of Compound (3a)

Into a 300-ml four-necked flask equipped with a thermometer, a calcium chloride tube and a stirrer was placed 12.5 g of Compound (2a) (purity: 90%, 22.5 millimole) and 70 ml of dehydrated diethylformamide was then added thereto and dissolved with stirring at room temperature. To this solution, the dimethylformamide solution of dimethyl chloroiminium chloride compound in Preparation Example 7 was added with ice cooling.

After the reaction mixture was further stirred at room temperature for 24 hours, it was poured into 1 liter of ice water. The separated crystal was filtered and then washed with a small amount of water, followed by vacuum drying to prepare 12.1 g of the desired compound (3a) (purity: 80% yield: 83%). This was identical with Example 1 in $^1$H NMR(DMSO) spectrum.

COMPARATIVE EXAMPLE 2

Preparation of Compound (3b):

Into a 300-ml four-necked flask equipped with a thermometer, a calcium chloride tube and a stirrer was placed 11.4 g of Compound (2b) (purity: 92%, 23.1 millimole) and 70 ml of dehydrated diethylformamide was then added thereto and dissolved with stirring at room temperature. To this solution, the dimethylformamide solution of dimethyl chloroiminium chloride compound in Preparation Example 7 was added with ice cooling.

The reaction mixture was treated in the same manner as in Comparative Example 2, to prepare 10.7 g of the desired compound (3b) (purity: 81%, yield: 80%). This was identical with Example 3 in $^1$H NMR(CDCl$_3$) spectrum.

INDUSTRIAL APPLICABILITY

In accordance with the invention, it is possible to overcome the drawbacks of long reaction time, unstable yield, low purity, and the formation of by-product obtained by halogenation of other than the desired hydroxyl group, which drawbacks being common to the methods of halogenating hydroxyl group by using dimethyl haloiminium compound or diphenyl haloiminium compound.

What is claimed is:

1. A halogenating agent of the formula (1)

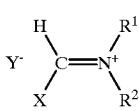 (I)

wherein R$^1$ and R$^2$ are the same or different and are each ethyl, propyl, isopropyl, butyl, isobutyl or allyl; X is chlorine atom or bromine atom; and Y is chlorine ion, bromine ion, dichlorophosphate ion, dibromophosphate ion, chlorosulfonate ion, bromosulfonate ion, chlorooxalate ion or bromooxalate ion.

2. A method of halogenating hydroxyl group comprising reacting in an organic solvent at least one of the halogenating agent of the formula (1) according to claim 1 with a hydroxyl group containing compound of the formula (2) to obtain a halogenide of the formula (3)

A—OH     (2)

wherein A is a straight-chain or branched-chain alkyl group which may be substituted, a straight-chain or branched-chain alkenyl-group which may be substituted, a monocyclic or polycyclic aromatic residue which may be substituted, a steroid residue, or a monocyclic or polycyclic heterocyclic residue which may be substituted

A—X     (3)

wherein A and X are the same as above.

3. A method of halogenating hydroxyl group as defined in claim 2 wherein the hydroxyl group containing compound (2) is at least one selected from the group consisting of the compounds (5) through (11)

compound (5): Sraight-chain or branched-chain alkyl alcohol in which alkyl part has 1 to 15 carbon atoms and may be substituted, compound (6): Straight-chain or branched-chain alkenyl alcohol in which alkenyl part has 2 to 8 carbon atoms and may be substituted, compound (7): 3-β-cholesterol, compound (8): compounds of the formula (8):

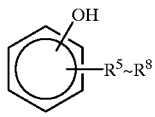
(8)

wherein $R^5$ to $R^8$ are the same or different and are each hydrogen atom, $C_1$–$C_4$ lower alkyl group, nitro group, hydroxyl group, carboxyl group, or substituted oxycarbonyl group, compound (9): compounds of the formulas (9a) to (9c):

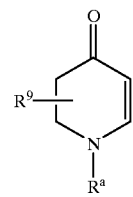
(9a)

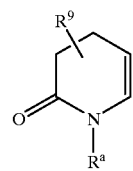
(9b)

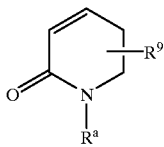
(9c)

wherein $R^9$ is a straight-chain or branched-chain $C_1$–$C_{15}$ alkyl group, a straight-chain or branched-chain $C_2$–$C_8$ alkenyl group, cyclohexyl group, or phenyl group; and Ra is hydrogen atom or a substituted oxycarbonyl group, compound (10): compounds of the formula (10):

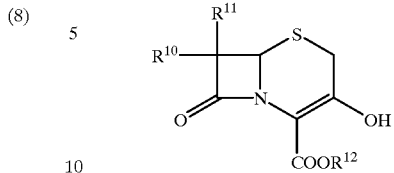
(10)

wherein $R^{10}$ is hydrogen atom, amino group, or a protected amino group; $R^{11}$ is hydrogen atom or lower alkoxy group, alternatively, $R^{10}$ and $R^{11}$ may be bonded with each other to form a cyclic amino protecting group; and $R^{12}$ is hydrogen atom or carboxylic acid protecting group, and compound (11): compounds of the formula (11):

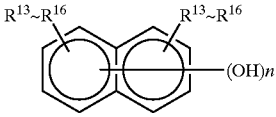
(11)

wherein $R^{13}$ to $R^{16}$ are the same or different and are each hydrogen atom, $C_1$–$C_4$ lower alkyl group, nitro group, hydroxyl group, carboxyl group, or a substituted oxycarbonyl group; and n is 1 or 2.

4. A method of halogenating hydroxyl group as defined in claim 3 wherein the hydroxyl group containing compound (2) is at least one selected from the group consisting of the compounds (5) through (10).

5. A method of halogenating hydroxyl group as defined in claim 4 wherein the hydroxyl group containing compound (2) is at least one selected from the group consisting of the compounds (7) to (10).

6. A method of halogenating hydroxyl group as defined in claim 5 wherein the hydroxyl group containing compound (2) is at least one selected from the group consisting of the compounds (9) and (10).

7. A method of halogenating hydroxyl group as defined in claim 6 wherein the hydroxyl group containing compound (2) is compound (10).

* * * * *